(12) United States Patent
Chung et al.

(10) Patent No.: US 6,370,409 B1
(45) Date of Patent: *Apr. 9, 2002

(54) POSITIONING METHOD FOR PULSE OXIMETRY FETAL SENSOR

(75) Inventors: Christopher Chung, Pleasanton, CA (US); Helen M. McNamara, Leeds (GB)

(73) Assignee: Nellcor Puritan Bennett, Inc., Pleasanton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/306,476

(22) Filed: May 6, 1999

Related U.S. Application Data

(60) Continuation of application No. 08/954,303, filed on Oct. 20, 1997, now Pat. No. 5,961,452, which is a continuation of application No. 08/406,761, filed on Mar. 17, 1995, now Pat. No. 5,743,260, which is a division of application No. 07/598,850, filed on Oct. 15, 1990, now Pat. No. 5,228,440.

(30) Foreign Application Priority Data

Aug. 22, 1990 (EP) ............................................. 90309180

(51) Int. Cl.$^7$ ................................................ A61B 5/00
(52) U.S. Cl. ....................................... 600/338; 600/339
(58) Field of Search ................................ 600/338, 310, 600/313, 322, 323, 339, 341, 342, 373, 376, 473, 476, 478

(56) References Cited

U.S. PATENT DOCUMENTS

| | | | |
|---|---|---|---|
| 3,167,658 A | 1/1965 | Richter | |
| 3,326,207 A | 6/1967 | Egan | |
| 3,599,629 A | 8/1971 | Gordy | |
| 3,602,213 A | 8/1971 | Howell et al. | |
| 3,647,299 A | 3/1972 | Lavallee | |
| 3,659,586 A | 5/1972 | Johns et al. | |
| 3,704,706 A | 12/1972 | Herczfeld et al. | |
| 3,769,974 A | 11/1973 | Smart et al. | |
| 3,841,314 A | 10/1974 | Page | |
| 3,983,866 A | 10/1976 | Ulrich et al. | |
| 4,013,057 A | 3/1977 | Kresse et al. | |
| 4,041,932 A | 8/1977 | Fostick | |
| 4,091,803 A | 5/1978 | Pinder | |
| 4,136,681 A | 1/1979 | Hon | |
| 4,197,853 A | 4/1980 | Parker | |
| 4,244,375 A | 1/1981 | Farrar et al. | |
| 4,281,659 A | 8/1981 | Farrar et al. | |
| 4,324,256 A | 4/1982 | Vesterager | |
| 4,350,165 A | 9/1982 | Striese | |
| 4,370,984 A | 2/1983 | Cartmell | |
| 4,396,017 A | 8/1983 | Delpy et al. | |
| 4,537,197 A | * 8/1985 | Hulka | |
| 4,658,825 A | 4/1987 | Hochberg | |
| 4,722,730 A | 2/1988 | Levy et al. | |

(List continued on next page.)

*Primary Examiner*—Eric F. Winakur
(74) *Attorney, Agent, or Firm*—Townsend and Townsend and Crew LLP

(57) ABSTRACT

An intrauterine pulse oximetry apparatus and method are provided to measure fetal blood oxygen saturation at sites in a preferred region on the fetus. The sensor of the apparatus is attached to a stiff cable which can be inserted into the uterus past the presenting part and transcervical region of the fetus. The cable may have visual and tactile markings by which the user, without seeing or feeling the sensor, can guide it to an appropriate site on the fetus.

24 Claims, 6 Drawing Sheets

U.S. PATENT DOCUMENTS

| | | | |
|---|---|---|---|
| 4,873,986 A | | 10/1989 | Wallace |
| 4,938,218 A | * | 7/1990 | Goodman et al. |
| 4,981,470 A | | 1/1991 | Bombeck, IV |
| 5,024,226 A | | 6/1991 | Tan |
| 5,025,787 A | | 6/1991 | Sutherland et al. |
| 5,099,842 A | | 3/1992 | Mannheimer et al. |
| 5,109,849 A | | 5/1992 | Goodman et al. |
| 5,135,006 A | * | 8/1992 | Bellinson |
| 5,154,175 A | | 10/1992 | Gunther |
| 5,218,962 A | | 6/1993 | Mannheimer et al. |
| 5,228,440 A | * | 7/1993 | Chung et al. |
| 5,247,932 A | | 9/1993 | Chung et al. |
| 5,361,757 A | | 11/1994 | Smith et al. |
| 5,377,675 A | | 1/1995 | Ruskewicz et al. |
| 5,411,024 A | | 5/1995 | Thomas et al. |
| 5,743,260 A | * | 4/1998 | Chung et al. |
| 5,961,452 A | * | 10/1999 | Chung et al. |

* cited by examiner

POSITIONING METHOD FOR PULSE OXIMETRY FETAL SENSOR

This is a continuation of application Ser. No. 08/954,303, filed Oct. 20, 1997, now U.S. Pat. No. 5,961,452, which is a continuation of application Ser. No. 08/406,761, filed Mar. 17, 1995, now U.S. Pat. No. 5,743,260, which is a Division of application Ser. No. 07/598,850, filed Oct. 15, 1990, now U.S. Pat. No. 5,228,440.

BACKGROUND OF THE INVENTION

This invention relates to an intrauterine pulse oximetry apparatus and method for measuring fetal oxygen saturation during labor and delivery. The invention particularly relates to placing the apparatus within a preferred region on the fetus.

A fetal pulse oximetry apparatus may include a sensor attached to an electrical cable. The sensor, which contains a light source and a light detector, is placed on the fetus. The cable connects the sensor to a pulse oximeter. Light from the light source is transmitted through the fetal tissue and reflected back to the light detector. The amount of light received by the light detector depends on characteristics of the blood in the fetal tissue, among other things.

Fetal pulse oximetry sensors are not new. Some previous apparatus were physically attached to the fetal skin by hooks, spirals, suction, or glue. One example is the fetal pulse oximetry sensor disclosed in PCT Publication No. WO 90/01293. These attachment means were invasive or potentially harmful. Therefore the apparatus were placed only in fetal regions that the doctor or other user could reach with his or her fingers, such as on the presenting part of the fetus or on the fetus within the uterine region just beyond the cervix (the "transcervical region").

The structure of previous apparatus did not permit safe and accurate placement on the fetus in the region beyond the reach of the user. In addition, nothing was known of fetal pulse characteristics in this region. Thus placement of the apparatus beyond the presenting part or in the transcervical region was considered undesirable.

SUMMARY OF THE INVENTION

Our tests have shown that fetal pulses are stronger in the region on the fetus beyond the presenting part and beyond the transcervical region. We call this fetal region the "preferred region." The present invention monitors pulses in the preferred region.

In a vertex presentation (the fetus descending headfirst), cervical pressure on the presenting part creates local edema (caput) which can suppress the fetal pulse and make pulse oximetry readings unreliable. The amplitude of the pulse in the presenting part also will change as the cervix dilates and changes the local force on the vertex.

During the periodic contractions of the uterine wall, additional local forces on the presenting part of the fetus are exerted actively by the cervix and passively by the pelvic bones. These transient local forces may further affect pulse amplitude. Thus, obtaining strong and consistent pulses throughout labor and delivery may be difficult.

The readings also may be affected by fetal hair. Depending on its color and amount, hair attenuates the light to various extents. Hair also may cause light to be shunted from the light source to the light detector, which adversely affects the measurement.

The present invention overcomes some of the shortcomings of previous fetal pulse oximetry apparatus and their placement methods. It provides an apparatus and a method of placing it in the preferred region, i.e. on the fetus beyond the presenting part and beyond the transcervical region. Pulse amplitudes in the preferred region are not affected by caput. They are less affected by cervical and pelvic bone forces than in the presenting part or the transcervical region. Since there is less hair (or even no hair) in the preferred region, the light transmission to and from the fetal tissue will be less attenuated and less susceptible to shunting. The apparatus and method allow the user to place the sensor without damaging the sensitive fetal eyes and fontanelles.

The preferred embodiment of the apparatus provides an electrical cable having a stiffer part adjacent to the sensor. This stiff part of the cable can be used to guide the sensor into position. The stiff part of the cable is rigid enough to be guided through the vagina and cervix without an introducer. It is flexible enough to yield when the sensor encounters an obstruction such as the uterine wall. With the sensor in position, the stiff part of the cable bends around the fetal head and conforms to the mother's pelvic curve. This conformance allows prolonged application of the sensor without discomfort to the mother.

The stiff part of the cable has calibrated visual markings and one or more tactile markings (ridges). The visual markings are particular distances from the leading edge of the sensor. The ridge is located at a position approximating the distance from the vertex of the fetal head to a site well within the preferred region on a fetus at term. The ridge may coincide with one of the visual markings.

Devices inserted into the mother's uterus must be sterile to avoid infection. As in prior art, the user must manipulate the apparatus within the vagina to place the sensor. If a prior-art device failed, the user would have to perform an additional vaginal examination to remove it. It would have to be sterilized before being reapplied. It also could be reapplied only with an introducer. If sterilizing were impractical, a new device would have to be used.

The current apparatus overcomes these limitations. If the sensor does not perform properly in its initial placement, the user can grasp the exposed stiff part of the cable and insert or withdraw it a small amount, for example 1 cm, as indicated by the visual markings. This action will reposition the sensor on a new site within the preferred region of the fetal head without removing the sensor from the uterus.

The method of using the apparatus has many advantages over prior art. It does not reintroduce anything into the vagina. Pulse oximetry readings thus can be taken without re-sterilizing the apparatus, outfitting it with an introducer, or using a new apparatus. The method typically is painless for the mother: it does not require uncomfortable manipulation of the apparatus inside the vagina. The method can be repeated during labor as necessary, for optimal sensor performance.

With the stiff part of the cable the user also can monitor the station of the fetal head (the position of the fetal head within the mother's pelvis). Fetal head station is important to evaluate the progression of labor. It is determined by internal examination, which assesses the position of the fetal head relative to the pelvic spines. The apparatus and method of the current invention permit the user to continuously assess this position without frequent repeated internal examinations.

As the fetal head descends during labor, the sensor descends with it. If the user notes the station of the fetal head when the sensor is initially placed, the station can be correlated with the amount of the stiff part of the cable protruding from the vagina. The visual markings indicate how much of the stiff part is exposed. The exposed stiff part of the cable will represent the station of the fetal head.

One skilled in the art will recognize that the apparatus could operate as a fetal station indicator without using the oximetry sensor so long as some means is provided of placing the inner end of the tube against the fetus within a preselected region. A trailer extending from the inner end of the indicator through the mother's vagina would have visual markings correlating to the station of the fetal head.

The objects of the invention are as follows:

To obtain improved pulse oximetry readings by measuring fetal oxygen saturation in a region with stronger pulses.

To obtain improved pulse oximetry readings by measuring fetal oxygen saturation in a region less affected by caput, cervical pressures, and hair.

To obtain the improved readings safely, that is without injuring the fetus or the mother.

To obtain the readings comfortably for the mother.

To allow prolonged yet comfortable and accurate monitoring of the fetus.

To orient the apparatus effectively without seeing or ultimately feeling the sensor, since the sensor's target is beyond the reach of the user.

To reposition the sensor in the preferred region without withdrawing the apparatus from the uterus.

When repositioning, to avoid re-sterilizing the apparatus.

When repositioning, to avoid using an introducer.

When repositioning, to avoid using a new (sterile) apparatus.

When repositioning, to avoid causing discomfort to the mother.

To determine the station of the fetal head during labor without repeated internal examinations.

BRIEF DESCRIPTION OF THE DRAWINGS

In all drawings, like parts are designated by like reference numbers.

FIG. 5 shows the user inserting the apparatus into the vagina.

FIG. 6 shows the user's hand guiding the sensor to the preferred region.

FIG. 7 shows the sensor in place in the preferred region after the user removed his or her hand.

DETAILED DESCRIPTION OF THE EMBODIMENTS

Figure 1:
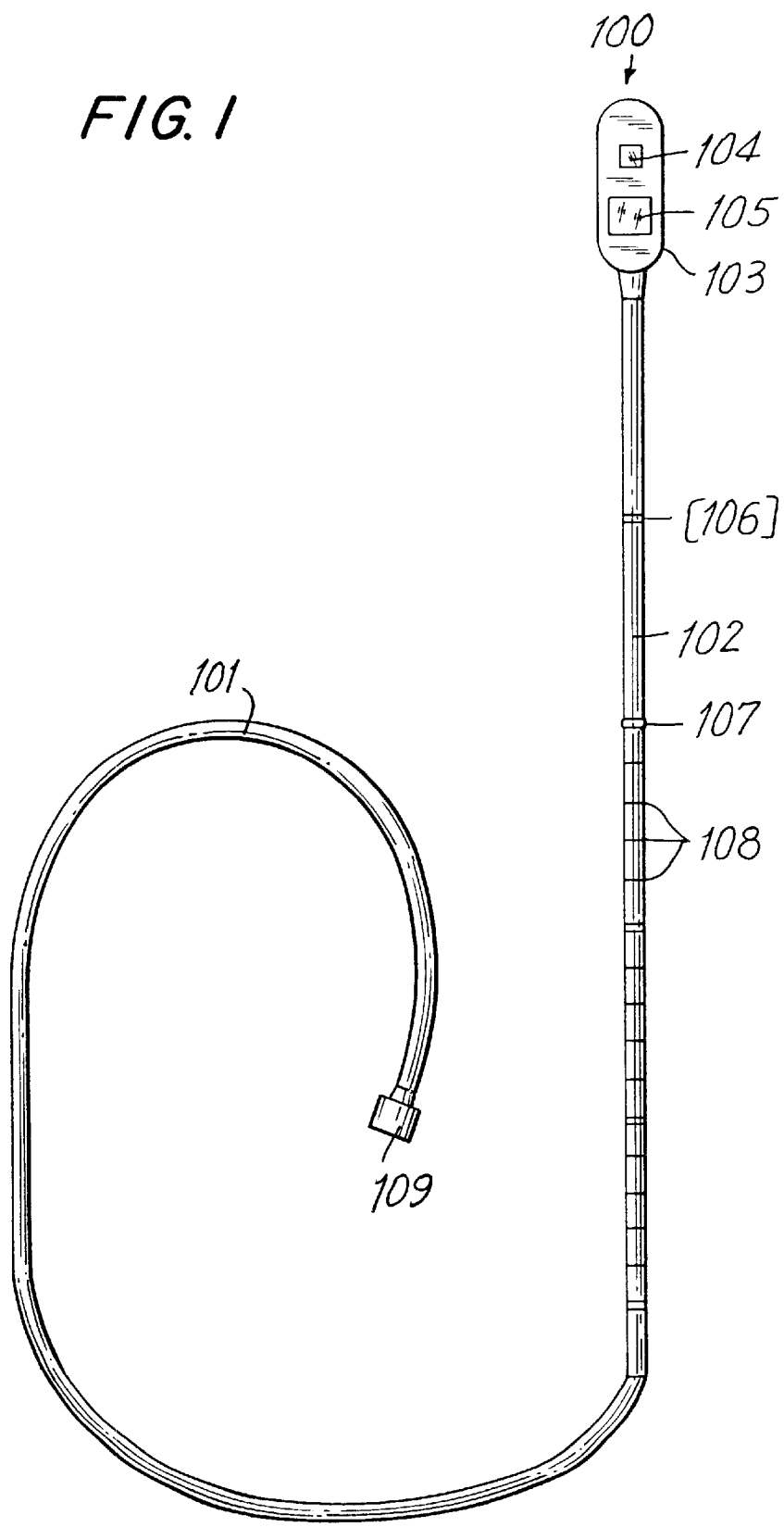
FIG. 1 is an overall view of the apparatus of the invention.

The preferred embodiment of the apparatus is shown in FIG. 1. Apparatus 100 includes a sensor 103 and an electrical cable 101 with a connector 109. The electrical cable has a stiffer part 102 adjacent to the sensor. The stiffer part of the cable is rigid enough to be guided unsupported through the vagina and cervix and flexible enough to yield when the sensor encounters an obstruction such as the uterine wall.

In the preferred embodiment, a part of the cable is stiffened by enclosing it in a plastic tube. For example, the cable can be surrounded by shrink-tubing of an inner diameter of 0.25 cm and an outer diameter of 0.41 cm. To allow repositioning, this tube must be long enough, preferably 30 cm, to extend from the vagina when the sensor is in the preferred region.

Figure 2:
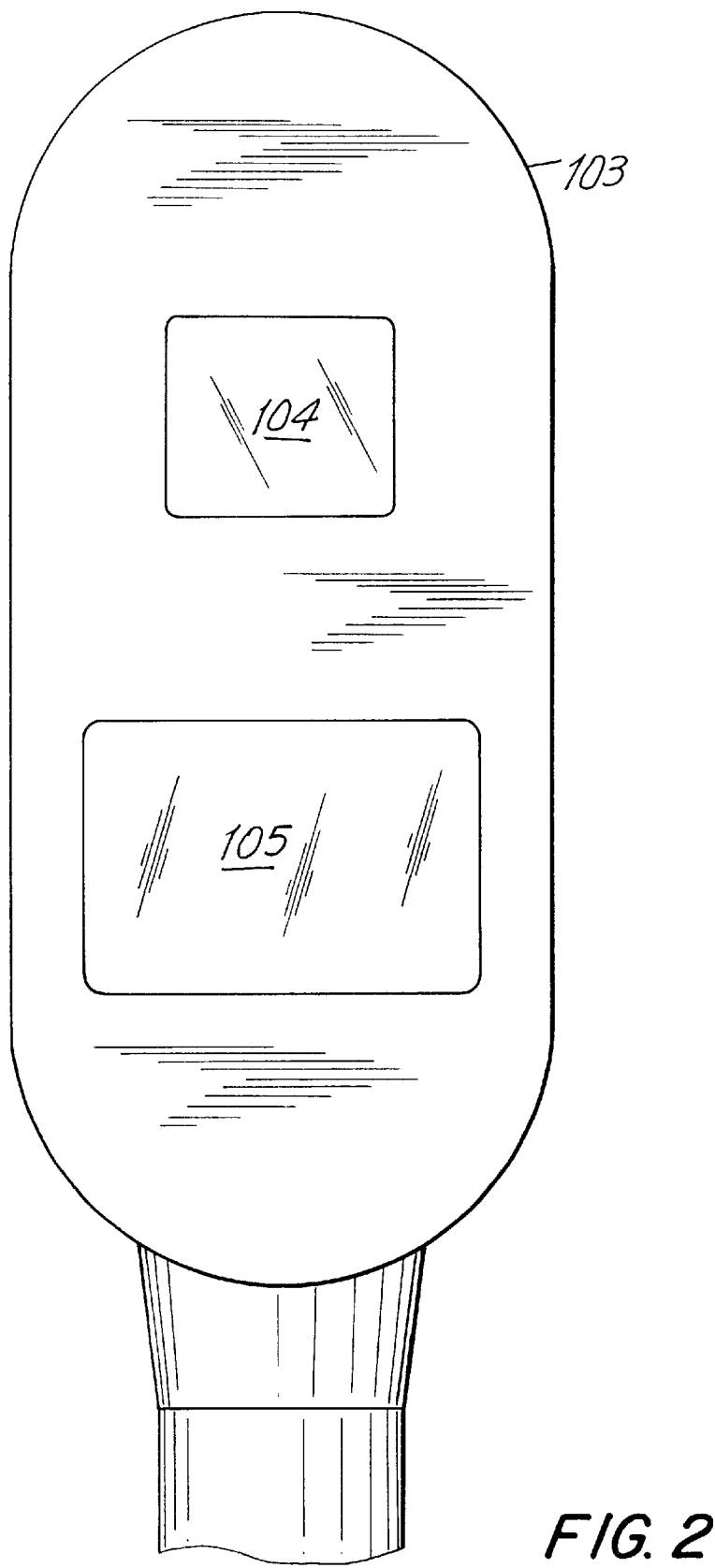
FIG. 2 is a view of the active side of the sensor, showing the light source and light detector.
Figure 3:
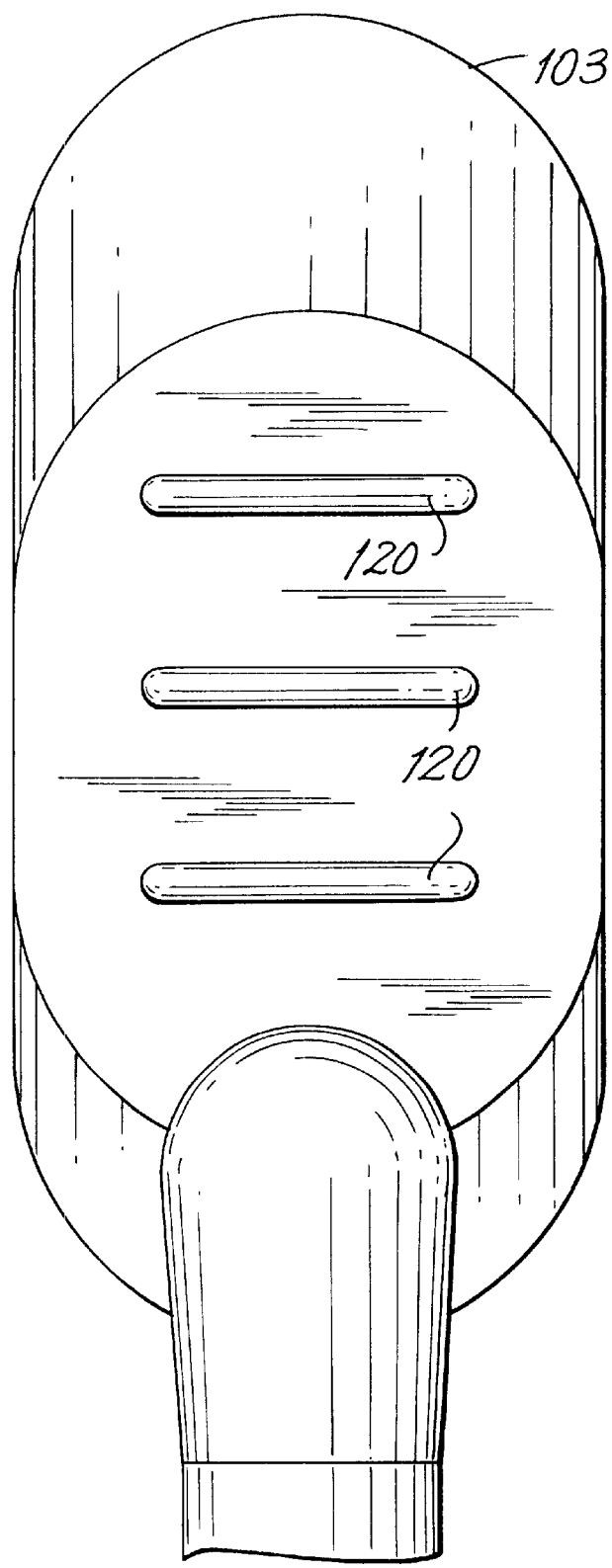
FIG. 3 is a view of the inactive side of the sensor.
Figure 4:
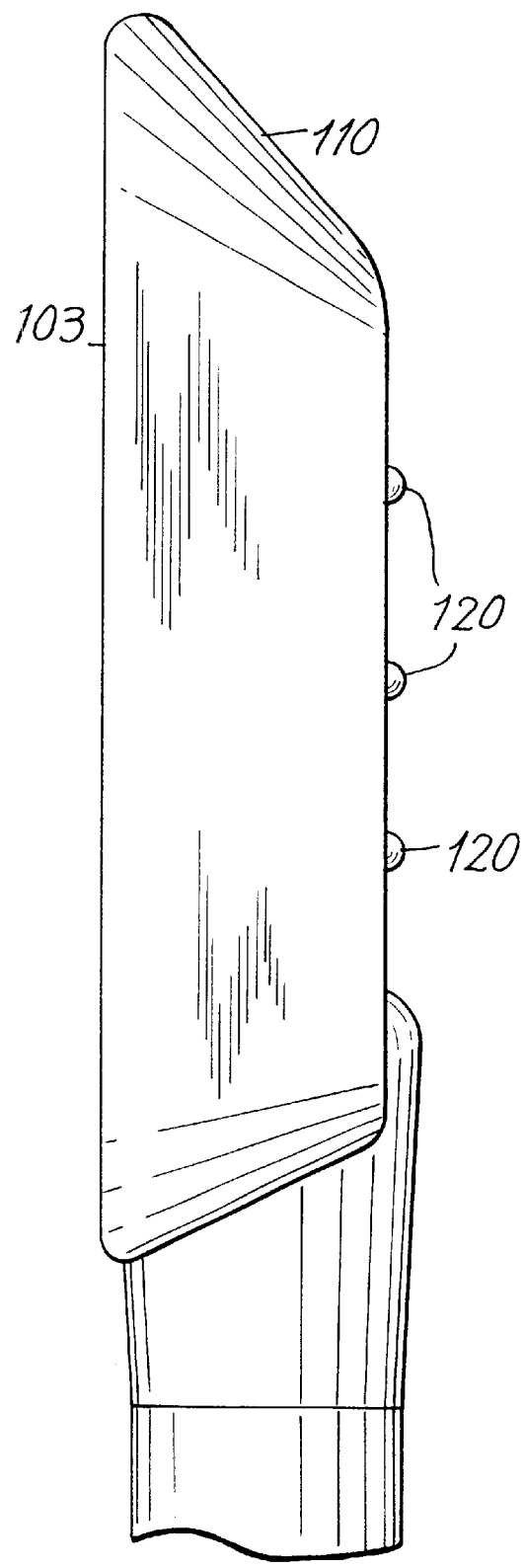
FIG. 4 is a cross-section of the sensor.

The sensor 103 has one or more emitters (the light source(s)) 104 and detectors (the light detector(s)) 105. The preferred embodiment has two emitters and a detector on one side, the active side, as shown in FIG. 2. In the preferred embodiment, the other or inactive side of the sensor has at least one tactile marking such as a bump or an indentation 120, as shown in FIGS. 3 and 4. This marking helps the user properly orient the apparatus while inserting it into the vagina and through the cervix. The leading edge 110 of the sensor 103 is bevelled, as shown in FIG. 4, to facilitate introduction later in labor through a cervix that may be well-applied to (snug against) the fetal presenting part 204.

The preferred embodiment of the cable 100 has a series of regularly spaced markings 108. These markings provide a visual indication of the insertion depth of the sensor in the mother's vagina. In addition, a ridge 107 is formed on the cable at a predetermined distance from the leading edge 110 of the sensor 103. The sensor is introduced until the ridge 107 is at the sagittal suture of the fetal head. The sensor is then in the preferred region 205.

The method of using the apparatus is as follows. The user determines the location of the fetal back and the height and orientation of the fetal head by abdominal examination. The user then makes a vaginal assessment of cervical status using the Bishop score. This score grades the cervix on five elements: dilatation, effacement, position, station (of the fetal head: above, below, or at the ischial spine), and consistency (firm, soft, etc.). The vaginal examination also may precisely confirm the position of the fetal head.

Figure 5:
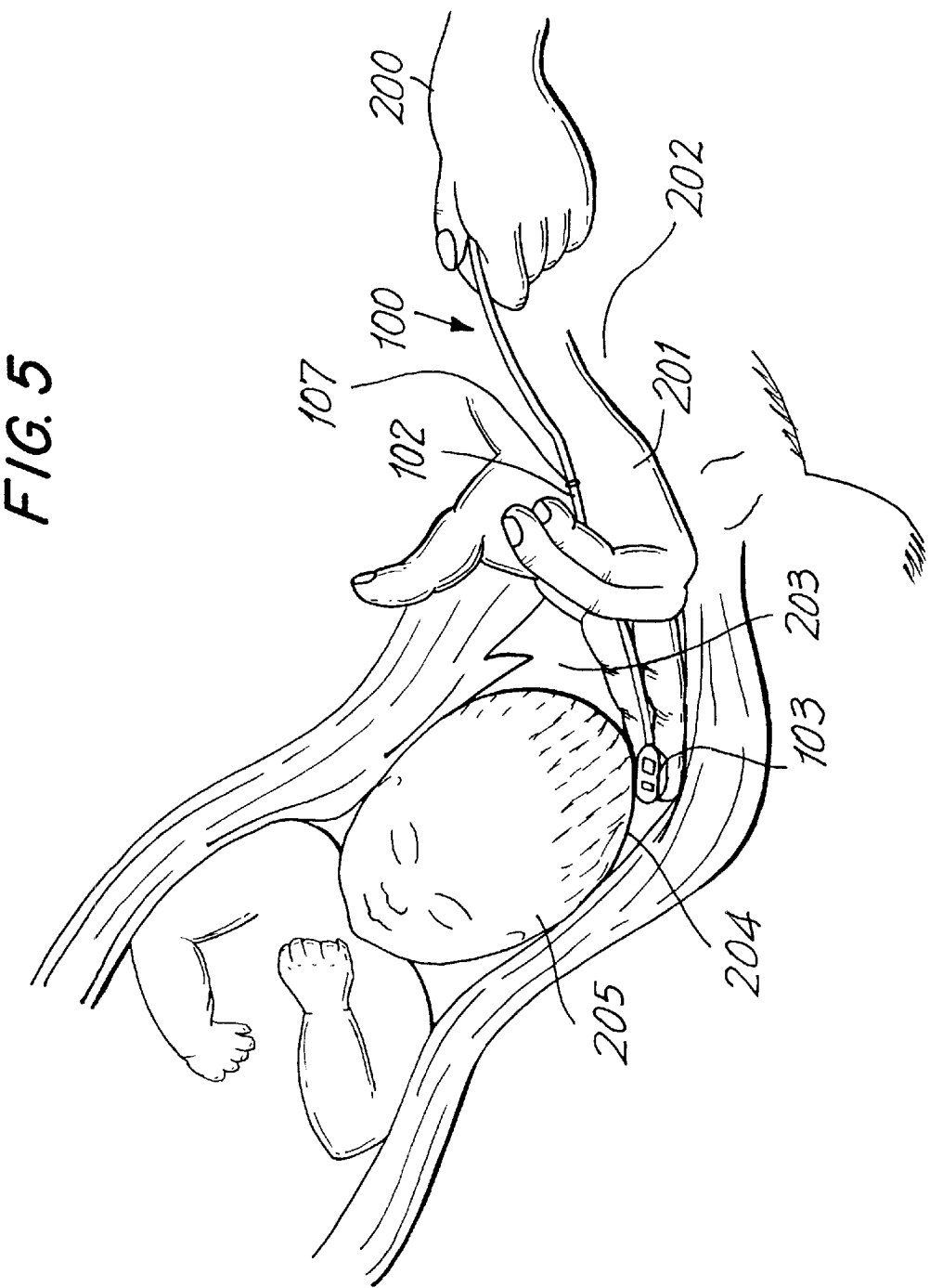
FIGS. 5 through 7 show the method of the invention.
Figure 6:
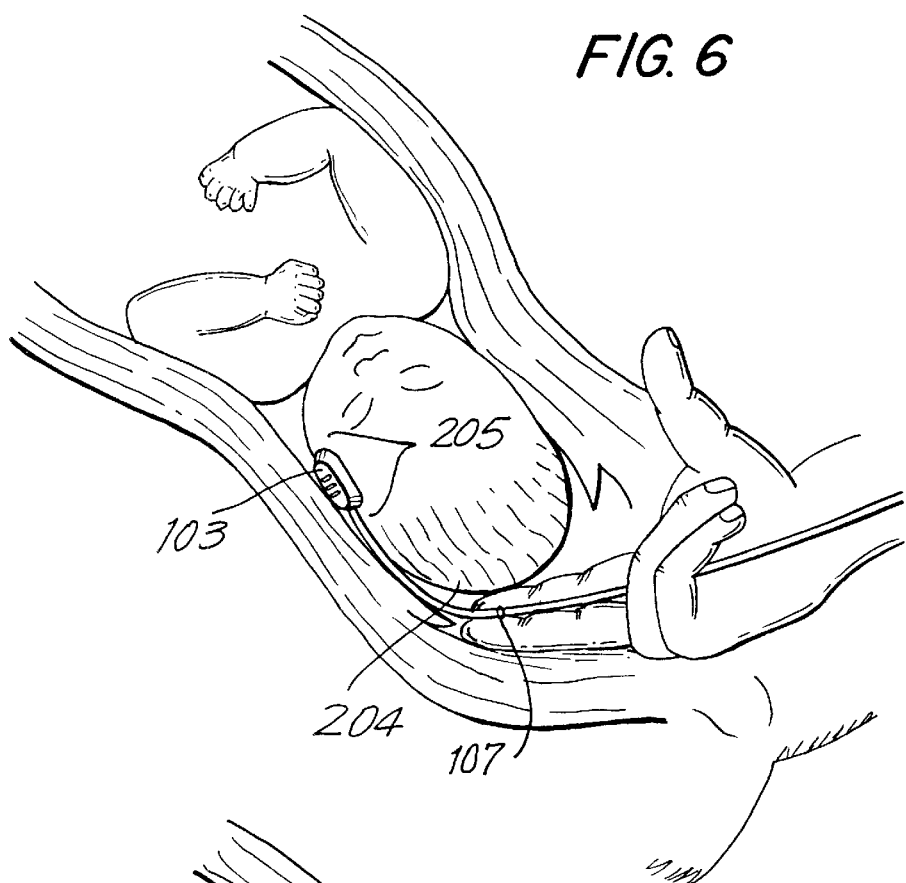

With the examining fingers 201 already in the vagina 202 and at the posterior cervix 203, the user grasps the apparatus 100 by the stiff part of the cable 102 with the other hand 200. The sensor 103 is then inserted into the vagina with the active side up. It is then threaded up between the index and middle fingers 201 of the examining hand. The finger-tips of that hand feel for the bump or indentation 120 on the inactive side of the sensor 103. See FIGS. 5, 6, and 7.

The fingers 201 of the examining hand stretch the posterior cervix 203 to make room for the sensor. The user further advances the sensor into the uterus past the presenting part and past the transcervical region. The sensor is then in the preferred region. For a fetus at term, the ridge 107 will be flush with the presenting part 204 when the sensor is in the preferred region, as in FIG. 6.

Figure 7:
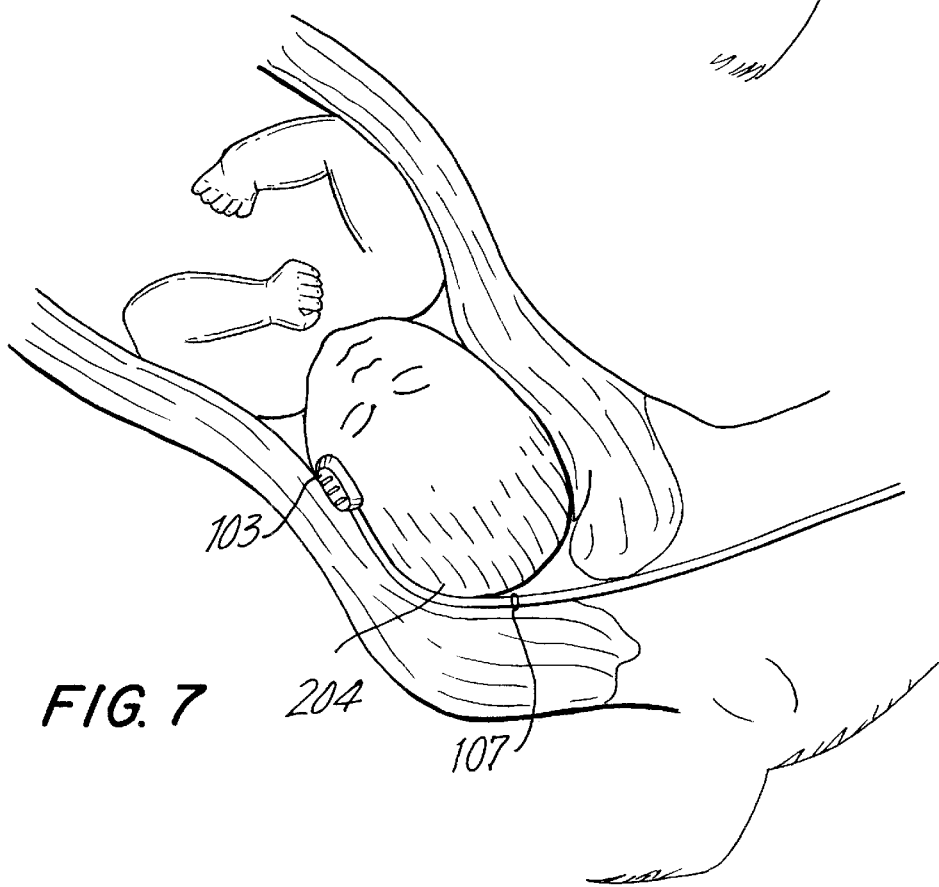

The user then removes his or her fingers from the vagina, leaving the sensor 100 in place, as in FIG. 7. If the readings from the initial placement are unsatisfactory, the sensor can be repositioned by slightly withdrawing or further inserting the stiff part of the cable 102.

The preferred method of constructing the cable's features is as follows. Plastic tubing, such as polyolefin made by Raychem, is heat-shrunk over the area of the cable to become the stiff part. This first layer stiffens the cable. Regularly spaced markings are then drawn on the plastic tubing. In the preferred embodiment the markings are 1 cm apart, although any convenient marking scale can be used. The markings can take various forms, such as colors, characters, or numbers.

The ridge is formed by heat-shrinking a short segment of plastic tubing around this cable assembly at an appropriate location. In the preferred embodiment, the ridge is 15 cm from the leading edge of the sensor. That is the approximate distance from the vertex of a molded fetal head at term to the preferred region for the sensor. The ridge may be used as a visual marking as well by making it a different color from that of the cable.

After the ridge and the visual markings are applied to the cable, a clear plastic sheath is heat-shrunk over the cable assembly. The sheath smoothes the edges of the ridge and protects the visual markings. It also further stiffens the cable.

We claim:

1. A fetal pulse oximetry apparatus comprising:
   a sensor including a light detector and a light source, said sensor being configured to contact a fetus without a positive attachment mechanism;
   means for conducting electrical signals to and from the sensor; and
   means for accurately placing the sensor at a site on the fetus beyond the presenting part and beyond the transcervical region.

2. The apparatus of claim 1 wherein the means for placing comprises a substantially stiff tube.

3. The apparatus of claim 2 wherein the tube encloses a part of the conducting means adjacent to the sensor.

4. The apparatus of claim 3 further comprising means for indicating the depth of insertion of the sensor into the vagina.

5. The apparatus of claim 4 wherein the means for indicating comprises visual markings on the tube.

6. The apparatus of claim 4 wherein the means for indicating comprises tactile markings on the tube.

7. The apparatus of claim 2 wherein the substantially stiff tube conforms to the pelvic curve.

8. The apparatus of claim 2 wherein the substantially stiff tube is enclosed in a clear sheath.

9. The apparatus of claim 1 wherein the sensor includes a tactile marker.

10. The apparatus of claim 1 wherein the leading edge of the sensor is bevelled.

11. The apparatus of claim 1 wherein the means for placing comprises means for stiffening, enabling the apparatus to remain straight enough under its own weight to be inserted unsupported into a vagina while bending slightly to avoid obstacles.

12. A method for measuring fetal oxygen saturation comprising the steps of:
   inserting a pulse oximetry sensor into the mother's vagina, said sensor being configured to contact a fetus without a positive attachment mechanism;
   moving the sensor through the cervix into the mother's uterus; and
   placing the sensor against the fetus at a site in a preferred region beyond the presenting part of the fetus and beyond the transcervical region.

13. The method of claim 12 wherein the preferred region is the fetal face.

14. The method of claim 12 wherein the preferred region is the fetal neck.

15. The method of claim 12 wherein the preferred region is the fetal scalp.

16. The method of claim 12 further comprising the step of placing an active side of the sensor on the fetus in the preferred region.

17. The method of claim 12 further comprising the step of using a tactile marker on one side of the sensor to orient the sensor.

18. The method of claim 12 further comprising the step of repositioning the sensor within the preferred region without removing the sensor from the uterus.

19. A method of measuring fetal oxygen saturation comprising the steps of:
   providing a pulse oximetry apparatus having a substantially stiff tube such that the tube remains straight enough under its own weight to be inserted unsupported into a vagina;
   providing a sensor at the insertion end of the stiff tube, said sensor being configured to contact a fetus without a positive attachment mechanism;
   inserting the sensor into the vagina; advancing the sensor through the cervix into the uterus; and
   placing the sensor on the fetus in a region beyond the reach of the user.

20. The method of claim 19 further comprising the step of using visual markings on the stiff tube to indicate the depth of the sensor in the vagina.

21. The method of claim 19 further comprising the step of using a tactile marking on the stiff tube to indicate the depth of the sensor in the uterus.

22. The method of claim 19 further comprising the step of using a tactile marking on the stiff tube to indicate the location of the sensor on the fetal head.

23. A method of measuring fetal oxygen saturation comprising the steps of:
   inserting a pulse oximeter sensor into the mother's vagina, said sensor being configured to contact a fetus without a positive attachment mechanism;
   moving out the sensor through the cervix into the mother's uterus; and
   placing the sensor against the fetus at a site in a region beyond the reach of the user.

24. A fetal station indicator comprising:
   a fetal sensor, said sensor being configured to contact a fetus without a positive attachment mechanism;
   means for placing a first end of the indicator within a preselected region on the fetus; and
   a trailer extending from the first end of the indicator, the trailer having visual markings, the trailer adapted to extend from the mother's vagina when the first end of the indicator is placed within the preselected region on the fetus.

* * * * *